United States Patent [19]
Bianchini

[11] 3,936,351
[45] Feb. 3, 1976

[54] METHOD FOR PREPARING GLUCORONYL-GLUCOSAMINO-GLYCAN SULPHATES EXHIBITING ANTILIPASAEMIC ACTIVITY

[75] Inventor: Pietro Bianchini, Modena, Italy

[73] Assignee: Opocrin S.r.l., Modena, Italy

[22] Filed: June 13, 1974

[21] Appl. No.: 479,036

[30] Foreign Application Priority Data
June 14, 1973 Italy................................ 25371/73

[52] U.S. Cl..................... 195/4; 195/7; 260/209 R; 260/211 R; 260/234 R; 424/104; 424/180
[51] Int. Cl.².................... A61K 35/38; C12D 3/00; C08B 37/00; A61K 31/70
[58] Field of Search........ 195/2, 4, 7, 6; 260/211 R, 260/211 AB, 209 R, 234; 424/104

[56] References Cited
UNITED STATES PATENTS

| | | | |
|---|---|---|---|
| 3,000,787 | 9/1961 | Bianchini............................ | 424/104 |
| 3,174,903 | 3/1965 | Fischer................................ | 424/104 |
| 3,810,978 | 5/1974 | Hamakawa et al.................. | 424/104 |

FOREIGN PATENTS OR APPLICATIONS

| | | | |
|---|---|---|---|
| 1,172,919 | 12/1969 | United Kingdom..................... | 195/4 |
| 889,010 | 2/1962 | United Kingdom............. | 260/211 R |

OTHER PUBLICATIONS

Bianchini, "Pancreatic Heparinoides," *Chemical Abstracts*, Vol. 72, pp. 250–251, 24600h, (1970).

Mihailescu, "Heparinoides," *Chemical Abstracts*, Vol. 70, p. 232, 60802t, (1969).

*Primary Examiner*—A. Louis Monacell

[57] ABSTRACT

Method for preparing glucuronyl-glucosamino-glycan sulphates exhibiting antilipasaemic activity, according to which the duodenum of pancreas of animals are subjected to a hydrolysis, the liquid is removed, precipitation is carried out with a quaternary ammonium, the precipitate is separated with a saline solution of NaCl, KCl or $CH_3COONa$, then filtering and adding the liquid with an alcohol causing the precipitation of the desired product.

5 Claims, No Drawings

METHOD FOR PREPARING GLUCORONYL-GLUCOSAMINO-GLYCAN SULPHATES EXHIBITING ANTILIPASAEMIC ACTIVITY

This invention relates to a method of extraction which makes it possible to obtain glucuronyl-glucosamino-glycan-sulphates with a high specific antilipemic action (10–20 U.LS/mg, where 1 U.LS. is the titre of the quantity of substance which, injected intravenously into a rate of 200 g., can induce after 10 minutes the release into the blood stream of lipoproteinolipases such as to cause a 50% fall in the optical density of a 1:2 mixture of the plasma with Ediol (Trade Mark), a 50% coconut oil emulsion, after 15' incubation in vitro).

These products are already used in therapy for their hypolipemic action, but preparations currently in use do not exceed 1 U.LS./mg: these are polysulphates, polysulphated and polycarboxylated mucopolysaccharides.

Extracting them requires a process of proteolysis or alkaline extraction in order to hydrolyse the protein-glycan complex and so liberate the polysaccharide part.

Some known processes for the preparation of glucuronyl-glucosamaino-glycan-sulphates with antilipemic action require successive precipitation with solvents of the material extracted, dissolving of the precipitate, and purification by various methods, such as resin column chromatography and/or selective precipitation of insoluble salts and complexes.

These processes, by their length and complexity, result in a considerable loss of material and time and in general a fairly low biological titre in the final product (about 1–2 U.LS./mg).

Examples of this type of process are described in British Pat. No. 1,172,919 and No. 889,010.

The fundamental aim of this invention is to realise a process which:

1. permits of directly obtaining products of a high degree of purity, with antilipemic action, free of anaphylaxis, histamine or pyrogens.

2. provides for selective precipitation of insoluble complexes in water in the phase immediately following proteolysis or alkaline hydrolysis on the animal organ treated and successive removal of impurities by washing the precipitate with a saline solution of the required concentration.

Such a process comprises the following steps:
- animal duodenum or pancreas is subjected to hydrolysis adding to these organs an aqueous solution of pH between about 5 and about 10 in the presence of an antibacterial agent acting exclusively as a bacterial flora inhibitor,
- the suspension is kept at 30°–70°C for up to 48 hours without contact with air and then heated to 70°–100°C for 10–40 minutes,
- the solid parts are separated, the method being characterised by the fact that the following steps are then taken:
- to the liquid obtained after separation is added an organic base with an aliphatic chain of at least 7 carbon atoms, in a quantity between 1% and 4% in weight of the weight of the animal organ treated and the liquid is brought to a pH between 7.5 and 8.5 with a 20–40% solution of an inorganic base,
- the liquid is heated to 70°–100°C for a period of 2 to 20 minutes, to increase the precipitate and encourage its centrifugation,
- the solid parts are separated from the liquid,
- the precipitate is washed first with distilled water and then with an aqueous saline solution with a molarity between 0.5 and 1,
- the precipitate is fractionated with an aqueous solution of the same salt used for the previous washing with a molarity between 2.5 and 4,
- the desired compound is precipitated from the solution using an alcohol having less than 4 carbon atoms with pH between 3 and 5.

The hydrolysis to which the animal organ (duodenum or pancreas) are subjected at the beginning of the process should preferably be an enzymatic hydrolysis effected by proteolytic enzymes such as pepsin, trypsin, papain etc. In this case the pH of the aqueous solution of the said animal organs should correspond to the optimum for the action of each type of enzyme used in the hydrolysis.

For greater clarity some examples of this method are now given, such examples not being limitative for the purposes of the protection claimed.

EXAMPLE 1

To 100 kg of minced swine duodenum are added 10 kg of NaCl, 400 g of NaOH and 200 liters of $H_2O$ giving a pH around 6–7. The suspension is kept boiling for 15–30 minutes and then cooled to 60°C. 1,500,000 I.U. of penicillin, 600 g of papain (1:100), 600 g of sodium hyposulphite are added and the whole is allowed to incubate for 16 hours at 60°C, after which the mixture is brought to the boil and kept boiling for 15–30 minutes. It is then centrifuged and the centrifuged liquid filtered.

To the perfectly clear liquid are added 3 liters of a quaternary ammonium base formed by a mixture composed of:
40% methyl dodecyl benzyl trimethyl ammonium chloride
10% methyl dodecyl xylylene bis(trimethyl ammonium chloride)
50% water The liquid is brought to pH 7.7 with NaOH at 30%, kept boiling for 5 minutes to give flocculation of the precipitate and centrifuged or filtered (the liquid is discarded).

The precipitate is washed twice with 20 liters of distilled $H_2O$ (and the washing water discarded) to remove excess mixture of any pyrogenic substances present in the precipitate which will form the product to be injected; the precipitate is then washed with 20 liters of a 0.8M NaCl solution (and the washing solution discarded) in order to remove substances weakly bound (carboxylic compounds) to the previously-used quaternary ammonium base which present no biological activity.

The precipitate is treated with 20 liters of a 3M NaCl solution to encourage fractionation of those substances only to which the activity is linked. Centrifugation is then carried out (solid matter being discarded) and the centrifuged liquid brought to pH 4.5 with glacial acetic acid.

1.5 volumes of methanol are added, the whole is centrifuged, and the centrifuged precipitate dissolved in 50 liters of a 2M NaCl solution and filtered until clear.

To the clear liquid, adjusted to pH 4, are added 1.5 volumes of methanol.

This is centrifuged and the precipitate washed twice with methyl alcohol and once with ethyl ether.

The precipitate is finally dried in vacuum: this operation gives the product to be injected, free of pyrogens, histamine and anaphylaxis, constituted of glucuronyl glucosamino glycan sulphates, with a clearing activity of approximately 20 U.LS.

The substance obtained also possesses an average content of: hexuronic acids, 180 mcg/mg; sulphates, 260 mcg/mg; hexosamines, 310 mcg/mg.

In the above example papain has been used as the proteolytic enzyme, but the process can be carried out with any other proteolytic enzyme, such as pepsin, trypsin, or chymotrypsin, adapting the ph and the working temperature to the enzyme used.

The same procedure as in the above example can be followed using reagents which are different but of the same type as those specified. For instance, the quaternary ammonium base added to the clear liquid may be n-alkyl (50% $C_{14}$ — 40% $C_{12}$ — 10% $C_{16}$) dimethyl benzyl ammonium chloride; the saline solution used for washing the precipitate may be a 0.5M KCl solution or a 1M $CH_3COONa$ solution; the aqueous solution used for fractionating the precipitate may be a 3.5M KCl aqueous solution or a 2.5M $CH_3COONa$ aqueous solution.

EXAMPLE 2

To 100 kg of minced bovine pancreas are added 15 kg of NaCl, 50 liters of $H_2O$, 1,500,000 I.U. of penicillin and NaOH up to pH 5 and the whole is left to incubate for 44 hours at about 40°C, resulting in autolysis of the pancreas.

The mixture is brought to the boil and kept boiling for 15 minutes, then centrifuged and filtered.

To the completely clear liquid, brought to pH 8.2 by KOH at 25%, is added 1 kg of trimethyl acetyl ammonium bromide. The mixture thus obtained is maintained for 10 minutes at about 80°C to help flocculation of the precipitate.

The liquid is then centrifuged and filtered (the liquid is discarded).

The precipitate is washed twice with 20 liters of distilled water (and the washing water discarded) and with 20 liters of a 0.5M KCl solution (washing solution is discarded).

The precipitate is then treated with 20 liters of a 4M KCl solution to encourage fractionation of those substances only to which the biological activity is linked.

The solution is then centrifuged (solid matter being discarded) and the opalescent liquid brought to pH 3.5 with HCl at 10%.

2 volumes of ethanol are added, the whole centrifuged, and the centrifuged precipitate washed twice with methyl alcohol and once with ethyl ether.

The precipitate is dried in vacuum; this operation gives a product which can be injected, free of pyrogens, histamine and anaphylaxis, constituted of glucuronyl glucosamino glycan sulphates, with a clearing activity of approximately 20 U.LS./mg.

The substance obtained also possesses an average content of: hexuronic acids, 270 mcg/mg; sulphates, 270 mcg/mg; hexosamines, 330 mcg/mg.

What we claim is:

1. A method of preparing glucosamino glycan sulphates with antilipaemic action comprising the steps of:
    subjecting animal duodenum or pancreas to hydrolysis, in a suspension an aqueous solution of pH between about 5 and about 10 in the presence of an antibacterial agent acting exclusively as a bacterial flora inhibitor,
    keeping the suspension at 30°–70°C for up to 48 hours without contact with air and then heating it to 70°–100°C for 10–40 minutes,
    separating off the solid parts,
    adding to the liquid obtained by separation an organic base having an aliphatic chain of at least 7 carbon atoms, in a quantity from 1% to 4% by weight of the weight of the animal organ treated, the liquid being then brought to pH from 7.5 to 8.5 with a 20–40% solution of an inorganic base,
    heating the liquid to 70°–100°C for from 2 to 20 minutes to increase the precipitate and prepare it for centrifugation,
    separating the solid parts from the liquid,
    washing the precipitate first with distilled water and then with a saline aqueous solution of molarity from 0.5 to 1,
    fractionating the precipitate with an aqueous solution of the same salt used for the previous washing with molarity from 2.5 to 4,
    precipitating the desired compound from the solution using an alcohol having 4 carbon atoms or less and pH from 3 to 5.

2. A method as claimed in claim 1, wherein the final compound precipitated is redissolved with a 1-3M saline solution, then clear filtered and finally precipitated to pH from 3 to 5 using an alcohol having 4 carbon atoms or less.

3. A method as claimed in claim 1, wherein the said hydrolysis is proteolytic enzymatic and the pH to which the said aqueous solution of the said animal organs is brought corresponds substantially to the optimum for activity of each type of enzyme used in the hydrolysis.

4. A method as claimed in claim 1, wherein the saline aqueous solution used for washing the precipitate is a 0.8M NaCl solution, a 0.5M KCl solution, or a 1M $CH_3COONa$ solution.

5. A method as claimed in claim 1, wherein the precipitate is fractionated with a saline aqueous solution consisting of a 3M NaCl solution, a 3.5M KCl solution, or a 2.5M $CH_3$ COONa solution.

* * * * *